United States Patent
Kim et al.

(10) Patent No.: US 11,261,431 B2
(45) Date of Patent: Mar. 1, 2022

(54) CRUSHED STEM CELL EXTRACT (SHELLED STEM CELL) MANUFACTURING METHOD USING MASS CULTURE MEDIUM COMPOSITION METHOD AND CONSTITUENT 3-LOW EXTRACTING METHOD AND A TREATING COMPOSITION FOR ANTI-INFLAMMATORY AND A TREATING COMPOSITION FOR CELL REGENERATION

(71) Applicant: Tiara Stem Cell Institute, Changwon-si (KR)

(72) Inventors: Young-Sil Kim, Changwon-si (KR); Jung-Eun Park, Changwon-si (KR); Hye-Jin Lee, Changwon-si (KR)

(73) Assignee: TIARA STEM CELL INSTITUTE, Changwon-si (KR)

( * ) Notice: Subject to any disclaimer, the term of this patent is extended or adjusted under 35 U.S.C. 154(b) by 183 days.

(21) Appl. No.: 16/038,595

(22) Filed: Jul. 18, 2018

(65) Prior Publication Data

US 2020/0002678 A1  Jan. 2, 2020

(30) Foreign Application Priority Data

Jun. 27, 2018  (KR) ........................ 10-2018-0074243

(51) Int. Cl.
*C12N 5/0775* (2010.01)
*A61K 35/545* (2015.01)
*A61K 9/16* (2006.01)

(52) U.S. Cl.
CPC .......... *C12N 5/0662* (2013.01); *A61K 9/1664* (2013.01); *A61K 35/545* (2013.01); *C12N 2500/25* (2013.01); *C12N 2500/32* (2013.01); *C12N 2500/44* (2013.01); *C12N 2501/117* (2013.01); *C12N 2501/148* (2013.01); *C12N 2501/15* (2013.01); *C12N 2501/165* (2013.01); *C12N 2501/33* (2013.01); *C12N 2501/905* (2013.01)

(58) Field of Classification Search
CPC ..................................................... C12N 5/0662
See application file for complete search history.

(56) References Cited

U.S. PATENT DOCUMENTS

| | | | |
|---|---|---|---|
| 8,353,619 B2 * | 1/2013 | Laugharn, Jr | G01N 1/286 366/127 |
| 8,846,061 B1 * | 9/2014 | Bezzek | A61K 8/41 424/400 |
| 9,993,504 B2 * | 6/2018 | Keller | A61K 35/32 |
| 10,233,479 B2 * | 3/2019 | Loo | G01N 35/00722 |
| 10,729,814 B2 * | 8/2020 | Kizer | A61L 27/3817 |

FOREIGN PATENT DOCUMENTS

KR   10-1561672 B1   10/2015

OTHER PUBLICATIONS

Yu et al. "Repair of Excitotoxic Neuronal Damage Mediated by Neural Stem Cell Lysates in Adult Mice". Journal of Cell Science and Therapy. 2011, vol. 2, Issue 3, pp. 1-5.*
Rajasingh et al. "Cell-Free Embryonic Stem Cell Extract-Mediated Derivation of Multipotent Stem Cells From NIH3T3 Fibroblasts for Functional and Anatomical Ischemic Tissue Repair", Circulation Research. 2008, 102: pp. e107-e117.*

* cited by examiner

*Primary Examiner* — Vera Afremova
(74) *Attorney, Agent, or Firm* — Paratus Law Group, PLLC

(57) ABSTRACT

Disclosed is a method of manufacturing a medium composition for cell culture, and a method of manufacturing a crushed stem cell extract using a method of manufacturing a medium composition for cell culture and a 3-low extracting method of active ingredients of a stem cell. The medium composition for cell culture includes a basal medium; a hyaluronic acid; and an additive composition. According to an embodiment, when active ingredients of a stem cell are extracted, a stem cell is crushed at a 3-low circumstance of low temperature, low pressure, a hypotonic circumstance.

1 Claim, 8 Drawing Sheets

CRUSHED STEM CELL EXTRACT (SHELLED STEM CELL) MANUFACTURING METHOD USING MASS CULTURE MEDIUM COMPOSITION METHOD AND CONSTITUENT 3-LOW EXTRACTING METHOD AND A TREATING COMPOSITION FOR ANTI-INFLAMMATORY AND A TREATING COMPOSITION FOR CELL REGENERATION

CROSS-REFERENCE TO RELATED APPLICATION

This application claims the priority benefit of Korean Patent Application No. 10-2018-0074243 filed on Jun. 27, 2018, the disclosure of which is incorporated herein by reference.

BACKGROUND

Embodiments of the invention relate to a method of manufacturing a medium composition for cell culture. More particularly, embodiments of the invention relate to a method of manufacturing a medium composition for cell culture being able to increase a yield of a stem cell by mass culture and a method of manufacturing a crushed stem cell extract using a method of manufacturing a medium composition for cell culture and a 3-low extracting method of active ingredients of a stem cell being able to increase a yield of active ingredients of a stem cell, and an anti-inflammatory composition and a cell-generation therapy composition using the same.

Stem cells are undifferentiated cells that can differentiate into various types of body tissues. By ability to differentiate into various tissue cells, many researches to stem cells have been conducted. Adult stem cells among stem cells are easily obtained from sites, such as fat, bone marrow, cord blood, placenta, or so on. Since there are few ethical issues in adult stem cells, compared to embryonic stem cells, and an immune rejection is less when user's own cells are used, there have been many studies regarding adult stem cells.

A treatment for directly injecting adult stem cells is limited to a self-treatment due to an immune rejection and the like. To overcome the limitation of the self-treatment, a removal of a membrane where immunogenicity that causes an immune rejection is attached through crushing stem cells is one of methods. The inventors of this application established a concept of the above-mentioned crushed stem cell extract and applied for a patent application for an original patent regarding the same. The advantage of the original patent is that there is universality that anyone can use the crushed stem cell extract by removing a membrane where immunogenicity that causes an immune rejection is attached. There is a reason for mass culture, and it contributes popularization and industrialization of stem cells as a result.

Thus, in order to achieve popularization and industrialization of stem cells, continuous research and development for methods useful for mass culture of stem cells and methods for extracting active ingredients of stem cells is required.

[Related Patent] Korea Patent No. 10-1561672

SUMMARY

Therefore, embodiments of the invention have been made in view of the above problems, and the invention is to provide a method of manufacturing a medium composition for cell culture being able to increase a yield of a stem cell by mass culture and a method of manufacturing a crushed stem cell extract using a 3-low extracting method of active ingredients of a stem cell being able to increase a yield of active ingredients of a stem cell.

In order to achieve the above object, a method of manufacturing a medium composition for cell culture includes: a basal medium; a hyaluronic acid; and an additive composition.

The additive composition may include at least one of glycine, histidine, isoleucine, methionine, phenylalanine, proline, hydroxyproline, serine, threonine, tryptophan, tyrosine, valine, bFGF, EGF, VEGF, KGF, HGF, TGF, vitamin C, vitamin B1, vitamin B12, vitamin E, selenium, and transferrin.

The basal medium may include one of DMEM (Dulbecco's Modified Eagle's Medium), MEM (Minimal Essential Medium), BME (Basal Medium Eagle), RPMI 1640, F-10, F12, DMEM-F12, α-MEM (α-Minimal Essential Medium), G-MEM (Glasgow's Minimal Essential Medium), IMDM (Iscove's Modified Dulbecco's Medium), MacCoy's 5A medium, AmnioMax, AmnioMax II complete Medium, Chang's Medium MesemCult-XF Medium.

In the additive composition, a concentration of the hyaluronic acid to the medium composition may be 10 μg/Ml, a concentration of the glycine to the medium composition may be 1 ng/Ml, a concentration of the histidine to the medium composition may be 1 ng/Ml, a concentration of the isoleucine to the medium composition may be 1 ng/Ml, a concentration of the methionine to the medium composition may be 1 ng/Ml, a concentration of the phenylalanine to the medium composition may be 1 ng/Ml, a concentration of the proline to the medium composition may be 10 ng/Ml, a concentration of the hydroxyproline to the medium composition may be 5 ng/Ml, a concentration of the serine to the medium composition may be 1 ng/Ml, a concentration of the threonine to the medium composition may be 1 ng/Ml, a concentration of the tryptophan to the medium composition may be 1 ng/Ml, a concentration of the tyrosine to the medium composition may be 1 ng/Ml, a concentration of the valine to the medium composition may be 2 ng/Ml, a concentration of the bFGF to the medium composition may be 9 μg/Ml, a concentration of the EGF to the medium composition may be 1.5 μg/Ml, a concentration of the VEGF to the medium composition may be 1 μg/Ml, a concentration of the KGF to the medium composition may be 1.2 μg/Ml, a concentration of the HGF to the medium composition may be 0.5 μg/Ml, a concentration of the TGF to the medium composition may be 0.5 μg/Ml, a concentration of the vitamin C to the medium composition may be 2 μg/Ml, a concentration of the vitamin B1 to the medium composition may be 0.5 μg/Ml, a concentration of the vitamin B12 to the medium composition may be 3 μg/Ml, a concentration of the vitamin E to the medium composition may be 500 μg/Ml, a concentration of the selenium to the medium composition may be 1.8 μg/Ml, or a concentration of the transferrin to the medium composition may be 12 μg/Ml.

Also, a method of manufacturing a crushed stem cell extract using a method of manufacturing a medium composition for mass culture of a stem cell and a 3-low extracting method of active ingredients of a stem cell includes: a first step of extracting a stem cell; a second step of culturing the extracted stem cell at the medium composition manufactured; a third step of subculturing the stem cell; a fourth step of obtaining a cell from the cultured stem cell; a fifth step of crushing the obtained cell; a sixth step of filtering the crushed material; and a seventh step of freeze-dehydrating the filtered material by the sixth step for storing or using the filtered material by the sixth step.

In the fifth step, an extracting apparatus of extracting the active ingredients of the stem cell may be used. The extracting apparatus may include: a body portion having an inner space and blocking an inside portion and an outer portion of the body portion; a first container provided in the body portion and opened upward; a second container having a size smaller than a size of the first container, wherein the second container provided in the first container and opened upward so that a stem cell is inserted into the second container; a crushing portion for crushing the stem cell in the second container; a valve for controlling or blocking a flow of air into the body portion; and a pump for sucking a gas in the body portion. The stem cell may be put into the second container in a state that the stem cell is put into a hypotonic solution.

According to another embodiment, an anti-inflammatory composition uses a crushed stem cell extract.

According to yet another embodiment, a cell-generation therapy composition uses a crushed stem cell extract.

According to still another embodiment, an anti-arthritis composition uses a crushed stem cell extract.

Effects of a method of manufacturing a medium composition for cell culture, and a method of manufacturing a crushed stem cell extract using a method of manufacturing a medium composition for cell culture and a 3-low extracting method of active ingredients of a stem cell are as follows.

It is stable without blood serum, and culture is increased by using a scaffold and thus a yield of effective factors or active ingredients of a stem cell can be increased.

When active ingredients of a stem cell are extracted, a stem cell is crushed at a 3-low circumstance of low temperature, low pressure, a hypotonic circumstance. Thus, the active ingredients of the stem cell can be prevented from being damaged.

Also, a membrane where immunogenicity that causes an immune rejection is attached can be completely removed by the crushed stem cell extract using the above two methods. Accordingly, there is universality that anyone can use the crushed stem cell extract and thus popularization and industrialization of stem cells can be achieved.

DETAILED DESCRIPTION

Hereinafter, a method for manufacturing a medium composition for cell culture, and a method of manufacturing a crushed stem cell extract using a method of manufacturing a medium composition for cell culture of a stem cell and a 3-low extracting method of active ingredients of a stem cell according to embodiments of the invention will be described in detail with reference to the accompanying drawings.

Figure 1:
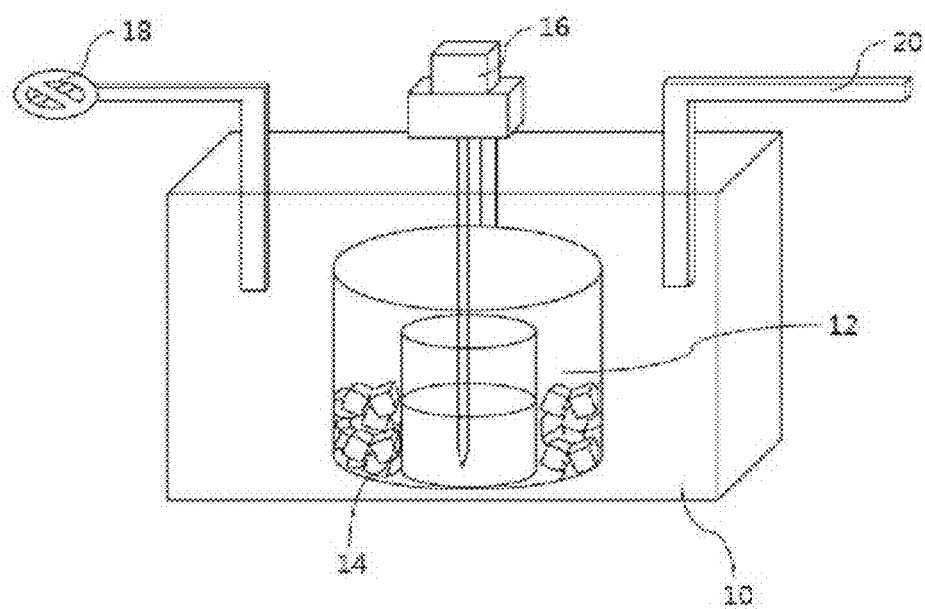
FIG. 1 shows a 3-low extracting apparatus of extracting active ingredients of a stem cell according to an embodiment of the invention.
Figure 2:
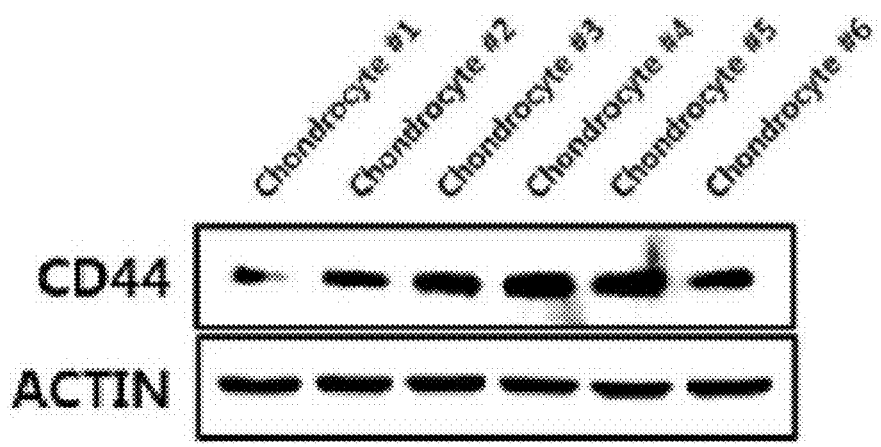
FIG. 2 shows a result of confirming a cartilage cell using CD44, which is a specific marker of a cartilage cell, in order to confirm an anti-arthritic effect of a crushed stem cell extract according to the invention.
Figure 3:
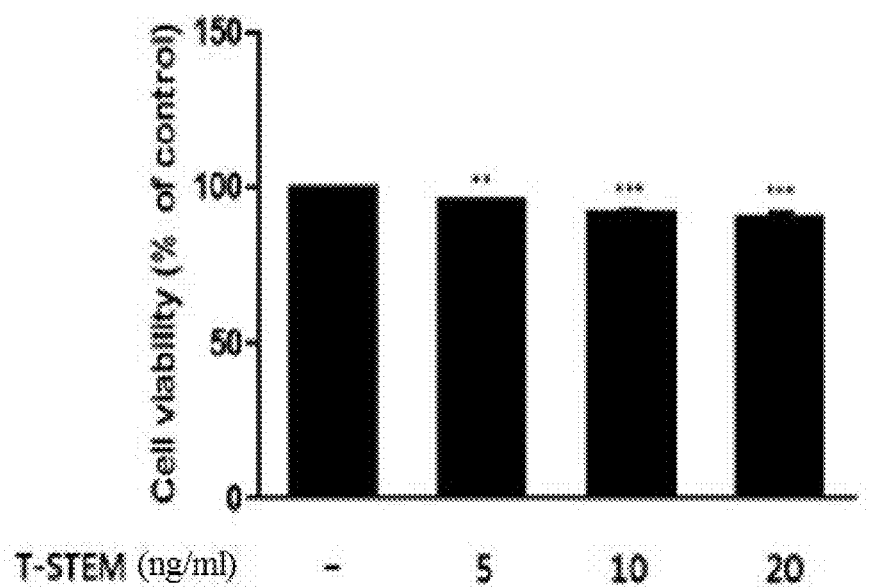
FIG. 3 shows a result of toxicity of materials by measuring cell viability after treating a cartilage cell with a crushed stem cell extract by concentration and culturing the same for 24 hours.
Figure 4:
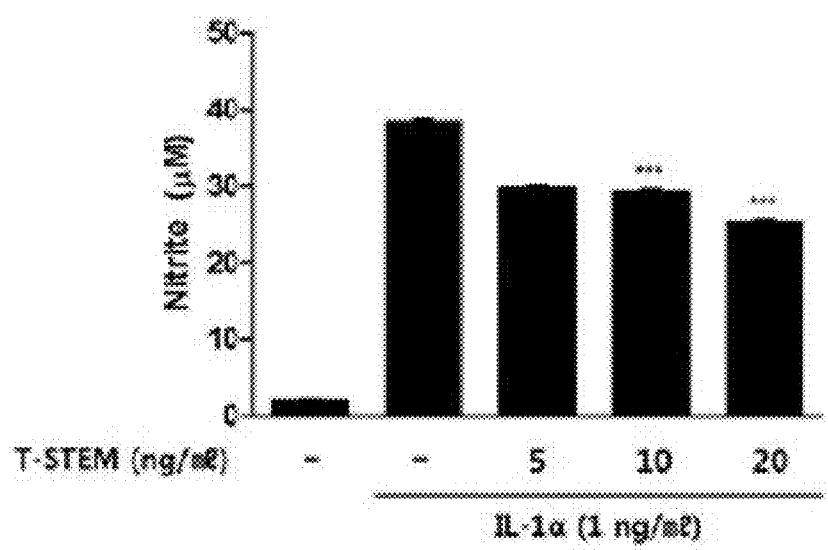
FIG. 4 shows a result of inhibition of NO generation, which is an inflammatory mediator, by treating IL-1α to a cartilage cell to cause inflammation and then treating the inflammatory cartilage cell with a crushed stem cell extract by concentration.
Figure 5:
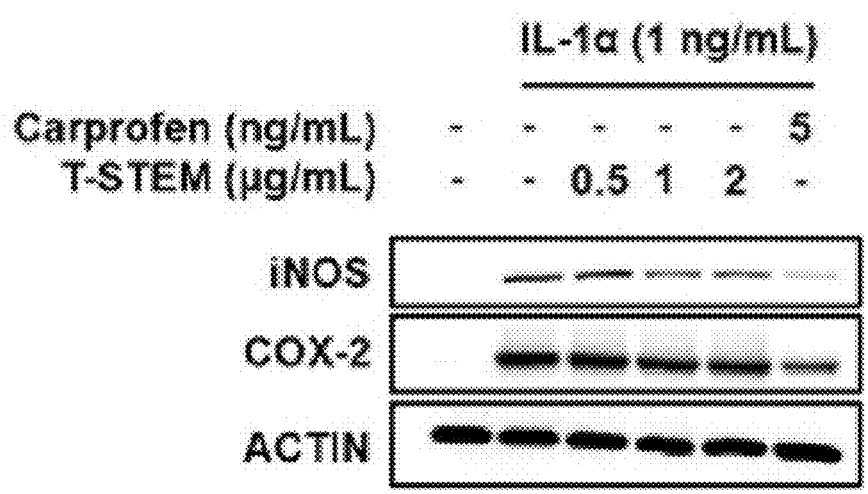
FIG. 5 shows a result for confirming a relation between inhibition effect of NO generation and inhibition of expression of iNOS and COX-2 by treating a cartilage cell with IL-1α to cause inflammation and then treating the inflammatory cartilage cell with a crushed stem cell extract.
Figure 6:
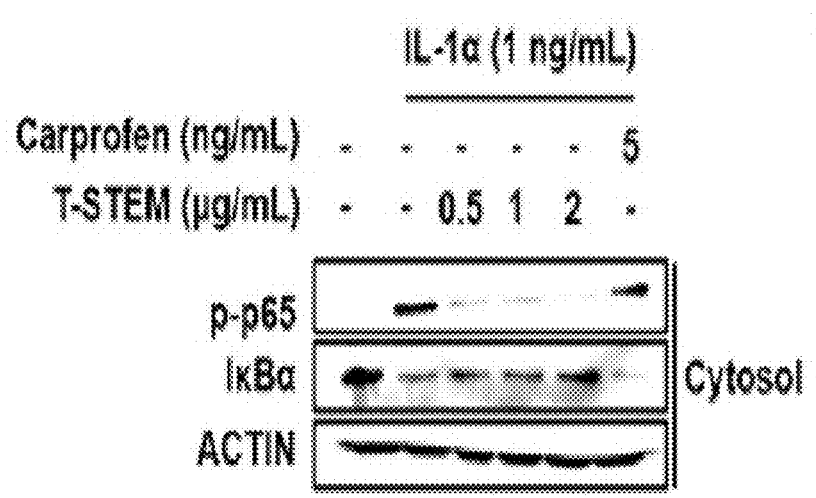
FIG. 6 shows that a migration of an NF-κB protein into a nucleus is inhibited in a cartilage cell treated with a crushed stem cell extract.
Figure 7:
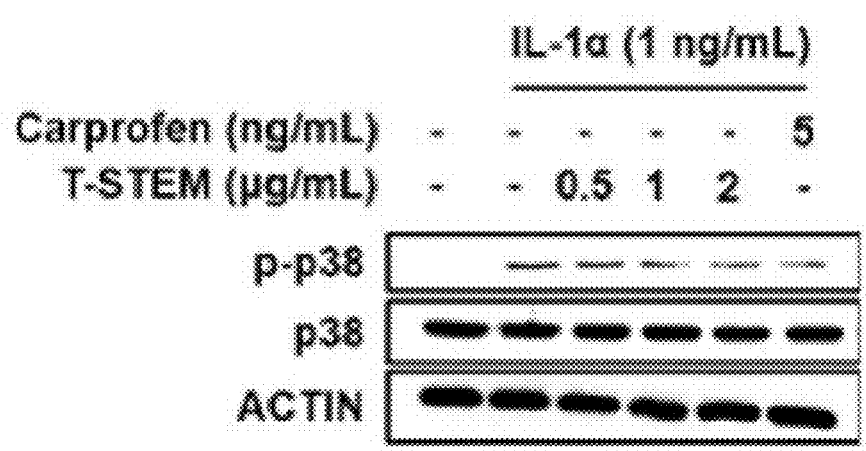
FIG. 7 shows an activity of IMAPKs by treating an inflammatory cartilage cell with IL-1α.
Figure 8:
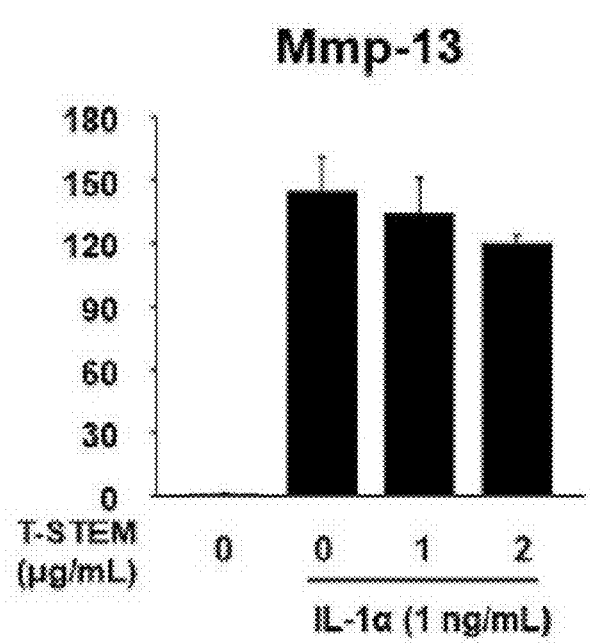
FIG. 8 shows anti-inflammatory effect of a crushed stem cell extract through genetic expression.
Figure 9:
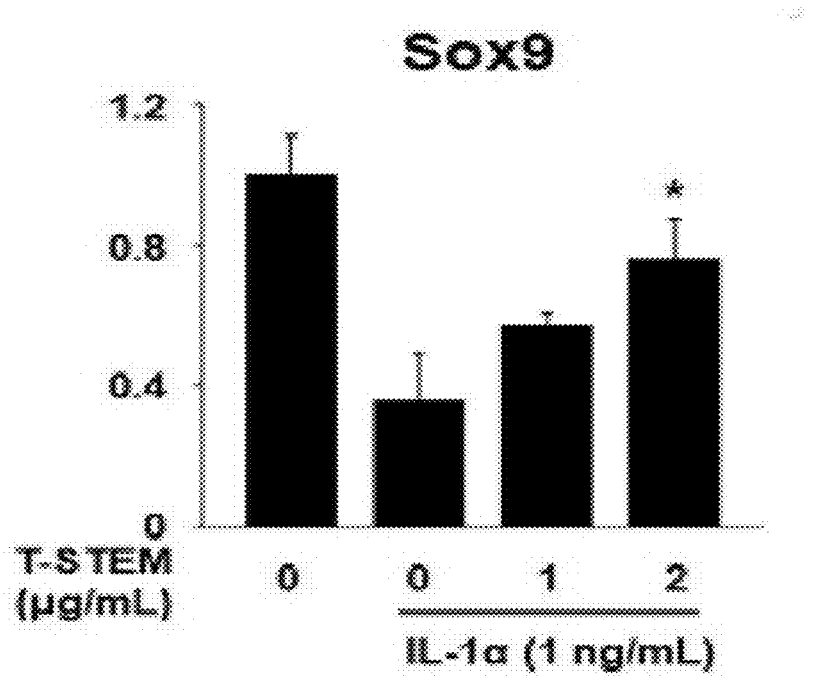
FIG. 9 shows effect of cartilage formation through a sox-9 gene involved in a cartilage formation and development.

As shown in FIG. 1, an extracting apparatus of extracting active ingredients of a stem cell according to an embodiment of the invention includes a body portion 10, a first container 12, a second container 14, a crushing portion 16, a valve 18, and a pump 20. The body portion 10 may have an inner space and block an inside portion and an outer portion of the body portion 10. The first container 12 may be provided in the body portion 10 and may be opened upward. The second container 14 may have a size smaller than a size of the first container 12 and may be provided in the first container 12. The second container 14 may be opened upward so that a stem cell is inserted into the second container 14. The crushing portion 16 crushes the stem cell in the second container 14, the valve 18 controls or blocks a flow of air into the body portion 10, and the pump 20 sucks the gas in the body portion 10.

First, the extracting apparatus according to the embodiment of the invention is provided with the body portion 10. As shown in FIG. 1, the body portion 10 is provided with an airtight or sealed space therein to block the outside portion and the inside portion thereof.

In the body portion 10, the first container 12 is provided. The first container 12 has a space therein and an upper portion of the first container 12 is opened. Ice is loaded in the first container 12 so that a temperature of the stem cell in the second container 14 is lowered to be described below.

The second container 14 is provided in the first container 12. The second container 14 has a space therein and an upper portion of the second container 14 is opened, similarly to the first container 12. Particularly, the second container 14 has a size smaller than that of the first container 12, and the second container 14 can be loaded in the first container 12. The stem cell may be loaded in the second container 14.

Further, the embodiment of the invention may further include the crushing portion 16. The crushing portion 16 serves to crush the stem cell loaded in the second container 14 by using ultrasonic waves.

In addition, the embodiment of the invention is provided with a passage through which air flows from the outside, and the valve 18 for selectively blocking a flow of air through the passage is provided. At the other end of the passage, the pump 20 is provided to discharge the air inside the body portion 10 to the outside so that the inside of the body portion 10 is evacuated.

In addition, the stem cell may be put into the second container 14 in a state that the stem cell is put into a hypotonic solution so that the stem cell is expanded. That is, the stem cell may be put into a hypotonic solution such as distilled water, and the stem cell may be expanded by osmotic pressure so that the stem cell is crushed by a small impact.

Also, a medium composition for mass culture of a stem cell and a method for manufacturing the same according to the invention will be described in detail.

In the invention, a new medium is manufactured to increase yield of a cell, and more active ingredients can be obtained when a cell or cells are crushed.

A basal medium of the medium may be a well known medium commonly used for culturing animal cells, for example, DMEM (Dulbecco's Modified Eagle's Medium), MEM (Minimal Essential Medium), BME (Basal Medium Eagle), RPMI 1640, F-10, F12, DMEM-F12, α-MEM (α-Minimal Essential Medium), G-MEM (Glasgow's Minimal Essential Medium), IMDM (Iscove's Modified Dulbecco's Medium), MacCoy's 5A medium, AmnioMax, AminoMax II complete Medium, Chang's Medium MesemCult-XF Medium, or the like, but the invention is not limited thereto.

Also, an additive composition may be added to the medium. The additive composition may include at least one selected from the group consisting of hyaluronic acid, glycine, histidine, isoleucine, methionine, phenylalanine, proline, hydroxyproline, serine, threonine, tryptophan, tyrosine, valine, bFGF (basic fibroblast growth factor), EGF (epidermal growth factor), VEGF (vascular endothelial growth factor), KGF (keratinocyte growth factor), HGF (hepatocyte growth factor), TGF (transforming growth factor), vitamin C, vitamin B1, vitamin B12, vitamin E, selenium, and transferrin.

First, the hyaluronic acid among the additive composition may be included. The hyaluronic acid acts as a scaffold during cell culture, and may be included at a concentration of 10 µg/ml to the medium composition.

And, the additive composition may include glycine. The glycine is an amino acid and serves as a nutrient for growth of cells. The glycine may be included at a concentration of 1 ng/ml to the medium composition.

The additive composition may include histidine. The histidine is an amino acid and serves as a nutrient for growth of cells. The histidine may be included at a concentration of 1 ng/ml to the medium composition.

The additive composition may include isoleucine. The isoleucine is an amino acid and serves as a nutrient for growth of cells. The isoleucine may be included at a concentration of 1 ng/ml to the medium composition.

The additive composition may include methionine. The methionine is an amino acid and serves as a nutrient for growth of cells. The methionine may be included at a concentration of 1 ng/ml to the medium composition.

The additive composition may include phenylalanine. The phenylalanine is an amino acid and serves as a nutrient for growth of cells. The phenylalanine may be included at a concentration of 1 ng/ml to the medium composition.

The additive composition may include proline. The proline is an amino acid and serves as a nutrient for growth of cells. The proline may be included at a concentration of 10 ng/ml to the medium composition.

The additive composition may include hydroxyproline. The hydroxyproline is an amino acid and serves as a nutrient for the growth of cells. The hydroxyproline may be included at a concentration of 5 ng/ml to the medium composition.

The additive composition may include serine. The serine is an amino acid and serves as a nutrient for growth of cells. The serine may be included at a concentration of 1 ng/ml to the medium composition.

The additive composition may include threonine. The threonine is an amino acid and serves as a nutrient for growth of cells. The threonine may be included at a concentration of 1 ng/ml to the medium composition.

The additive composition may include tryptophan. The tryptophan is an amino acid and serves as a nutrient for growth of cells. The tryptophan may be included at a concentration of 1 ng/ml to the medium composition.

The additive composition may include tyrosine. The tyrosine is an amino acid and serves as a nutrient for growth of cells. The tyrosine may be included at a concentration of 1 ng/ml to the medium composition.

The additive composition may include valine. The valine is an amino acid and serves as a nutrient for growth of cells. The valine may be included at a concentration of 2 ng/ml to the medium composition.

And, the additive composition may include bFGF. The bFGF assists in a growth of cells to be cultured, and may be included at a concentration of 9 µg/ml to the medium composition.

The additive composition may include EGF. The EGF assists in a growth of cells to be cultured and may be included at a concentration of 1.5 µg/ml to the medium composition.

The additive composition may include VEGF. The VEGF helps to grow cells to be cultured, and may be included at a concentration of 1 µg/ml to the medium composition.

The additive composition may include KGF. The KGF assists in the growth of cells to be cultured, and may be included at a concentration of 1.2 µg/ml to the medium composition.

The additive composition may include HGF. The HGF helps to grow the cells to be cultured, and may be included at a concentration of 0.5 µg/ml to the medium composition.

The additive composition may include TGF. The TGF assists in a growth of cells to be cultured, and may be included at a concentration of 0.5 µg/ml to the medium composition.

And, the additive composition may include vitamin C. The vitamin C helps to grow cells to be cultured, and may be included at a concentration of 2 µg/ml to the medium composition.

The additive composition may include vitamin B1. The vitamin B1 assists in a growth of cells to be cultured, and may be included at a concentration of 0.5 μg/ml to the medium composition.

The additive composition may include vitamin B12. The vitamin B12 helps to grow cells to be cultured and may be included at a concentration of 3 μg/ml to the medium composition.

The additive composition may include vitamin E. The vitamin E assists in a growth of cells to be cultured, and may be included at a concentration of 500 μg/ml to the medium composition.

And, the additive composition may include selenium. The selenium assists in an activation of cells, and may be included at a concentration of 1.8 μg/ml to the medium composition.

The additive composition may include transferrin. The transferrin assists in an activation of cells and may be included at a concentration of 12 μg/ml to the medium composition.

Hereinafter, a method of manufacturing a medium composition for cell culture, and a method of manufacturing a crushed stem cell extract using a method of manufacturing a medium composition for cell culture and a 3-low extracting method of active ingredients of a stem cell, using an extracting apparatus of extracting active ingredients of a stem cell according to the invention, will be described.

First Step: A stem cell or stem cells are extracted from any one of human fat, bone marrow, cord blood, or placenta. In the invention, fat is collected by liposuction, and a fat stem cell of the fat is separated and purified by enzyme treatment and centrifugation several times.

Second Step: The separated stem cell or stem cells are cultured using a culture medium manufactured by using the medium composition for mass culture of the invention described above. When the medium composition for mass culture of the stem cell is used, a growth rate of the stem cell can be increased and a yield of the stem cell can be increased.

Third Step: After the culture medium (the culture fluid) in which the stem cell has been cultured is removed, the stem cell or the stem cells are separated and a cell suspension is obtained and subcultured.

Fourth Step: When the cell or the cells grow to have a sufficient density, the cell is separated from a plate. After the stem cell is separated, the stem cell is washed several times with physiological saline or PBS (phosphate buffer saline). A number of cells are counted by using a cell counting device to make a suspension at a constant concentration.

Fifth Step: A supernatant is removed and an extender is added to allow to crush a stem cell membrane. Ultrasonic waves are applied to the cells and the cells are crushed by a 3-low extracting method of active ingredients of a stem cell. When it is confirmed that all the stem cells are crushed through a microscope, the crush is terminated. By the 3-low extracting method, the cell membrane can be effectively crushed in a short time, and thus, most of active ingredients such as growth factors and cell active materials in the stem cells are maintained.

Sixth Step: There are cell membrane residues along with various growth factors and cellular active substances, which are materials of the stem cell contents, in a mixture of a hypotonic expander and the crushed stem cell. Among them, unnecessary cell membrane residues are removed by using centrifugation and a fine filter. In this instance, immunogenicity that is attached to the cell membrane and causes an immune rejection is removed, and available active ingredients of the stem cell are extracted.

Seventh Step: The crushed stem cell extract obtained through the above is stored frozen or freeze dried (freeze dehydrated), and is used.

The active ingredients obtained through the above steps are called a crushed stem cell extract or are called a shelled stem cell.

Hereinafter, experimental results of active ingredients of a crushed stem cell extract using a medium composition for mass culture of a stem cell including an additive composition according to the invention will be shown or described.

Comparative Example 1

Stem cells were cultured in a medium where 100 parts by weight of DMEM (Dulbecco's Modified Eagle Medium), 11.12 parts by weight of FBS added as blood serum, and 0.6 parts by weight of penicillin as antibiotics were mixed with each other, were grown in the same manner as described above, and active ingredients (or active factors) were extracted.

Embodiment 2

Stem cells were cultured in a medium in which 100 parts by weight of DMEM (Dulbecco's Modified Eagle Medium) and 20 parts by weight of serum including nutrient materials were mixed and blood serum is not included, were grown in the same manner as described above, and active ingredients were extracted.

Embodiment 3

Stem cells were cultured in a medium in which 100 parts by weight of DMEM (Dulbecco's Modified Eagle Medium) and 5 parts by weight of an additive composition of the invention shown in Table 1 were mixed with, were grown in the same manner as described above, and active ingredients were extracted.

Embodiment 4

Stem cells were cultured in a medium in which 100 parts by weight of DMEM (Dulbecco's Modified Eagle Medium) and 10 parts by weight of an additive composition of the invention shown in Table 1 were mixed with, were grown in the same manner as described above, and active ingredients were extracted.

Embodiment 5

Stem cells were cultured in a medium in which 100 parts by weight of DMEM (Dulbecco's Modified Eagle Medium) and 15 parts by weight of an additive composition of the invention shown in Table 1 were mixed with each other, were grown in the same manner as described above, and active ingredients were extracted.

Embodiment 6

Stem cells were cultured in a medium in which 100 parts by weight of DMEM (Dulbecco's Modified Eagle Medium) and 20 parts by weight of an additive composition of the invention shown in Table 1 were mixed with each other, were grown in the same manner as described above, and active ingredients were extracted.

Embodiment 7

Stem cells were cultured in a medium in which 100 parts by weight of DMEM (Dulbecco's Modified Eagle Medium) and 25 parts by weight of an additive composition of the invention shown in Table 1 were mixed with each other, were grown in the same manner as described above, and active ingredients were extracted.

Embodiment 8

Stem cells were cultured in a medium in which 100 parts by weight of DMEM (Dulbecco's Modified Eagle Medium) and 30 parts by weight of an additive composition of the invention shown in Table 1 were mixed with each other, were grown in the same manner as described above, and active ingredients were extracted.

Embodiment 9

Stem cells were cultured in a medium in which 100 parts by weight of DMEM (Dulbecco's Modified Eagle Medium) and 35 parts by weight of an additive composition of the invention shown in Table 1 were mixed with each other, were grown in the same manner as described above, and active ingredients were extracted.

Embodiment 10

Stem cells were cultured in a medium in which 100 parts by weight of DMEM (Dulbecco's Modified Eagle Medium) and 40 parts by weight of an additive composition of the invention shown in Table 1 were mixed with each other, were grown in the same manner as described above, and active ingredients were extracted.

Embodiment 11

Stem cells were cultured in a medium in which 100 parts by weight of DMEM (Dulbecco's Modified Eagle Medium) and 45 parts by weight of an additive composition of the invention shown in Table 1 were mixed with each other, were grown in the same manner as described above, and active ingredients were extracted.

Embodiment 12

Stem cells were cultured in a medium in which 100 parts by weight of DMEM (Dulbecco's Modified Eagle Medium) and 50 parts by weight of an additive composition of the invention shown in Table 1 were mixed with each other, were grown in the same manner as described above, and active ingredients were extracted.

TABLE 1

| Classification | Material | Concentraion | |
|---|---|---|---|
| Scaffold | hyaluronic acid | 10 | µg/ml |
| Amino Acid | glycine | 1 | ng/ml |
| | histidine | 1 | ng/ml |
| | isoleucine | 1 | ng/ml |
| | methionine | 1 | ng/ml |
| | phenylalanine | 1 | ng/ml |
| | proline | 10 | ng/ml |
| | hydroxyproline | 5 | ng/ml |
| | serine | 1 | ng/ml |
| | threonine | 1 | ng/ml |
| | tryptophan | 1 | ng/ml |
| | tyrosine | 1 | ng/ml |
| | valine | 2 | ng/ml |
| Growth Factor | bFGF | 9 | µg/ml |
| | EGF | 1.5 | µg/ml |
| | VEGF | 1 | µg/ml |
| | KGF | 1.2 | µg/ml |
| | HGF | 0.5 | µg/ml |
| | TGF | 0.5 | µg/ml |
| Vitamin | vitamin C | 2 | µg/ml |
| | vitamin B1 | 0.5 | µg/ml |
| | vitamin B12 | 3 | µg/ml |
| | vitamin E | 500 | µg/ml |
| Trace Element (Microelement) | selenium | 1.8 | ng/ml |
| | transferrin | 12 | µg/ml |

Next, an experimental result showing an amount of obtained cells by culturing the cells using the medium composition for cell culture according to the invention will be described.

TABLE 2

| Measurement Type | | Obtained before cell crushing |
|---|---|---|
| Detention Amount (Average) | Group | Amount of obtained cells (number/ml) |
| | Control Group | $1.1 \times 10^4$ |
| | Comparative Example 1 | $2.3 \times 10^5$ |
| | Embodiment 1 | $8.7 \times 10^5$ |
| | Embodiment 2 | $8.6 \times 10^5$ |
| | Embodiment 3 | $8.9 \times 10^5$ |
| | Embodiment 4 | $9.3 \times 10^5$ |
| | Embodiment 5 | $9.7 \times 10^5$ |
| | Embodiment 6 | $1.2 \times 10^6$ |
| | Embodiment 7 | $1.5 \times 10^6$ |
| | Embodiment 8 | $1.8 \times 10^6$ |
| | Embodiment 9 | $2.1 \times 10^6$ |
| | Embodiment 10 | $2.4 \times 10^6$ |
| | Embodiment 11 | $2.5 \times 10^6$ |
| | Embodiment 12 | $2.5 \times 10^6$ |

As shown in Table 2, it can be seen that amounts of obtained cells in Examples 2 to 12 are high. However, it can be seen that the amount of obtained cells in Example 2 is similar to that in Example 1 in which the blood serum is added. Also, it can be seen that an increase degree in the amounts of obtained cells in Example 11 and Example 12 is relatively low and efficiency in obtaining cell is low.

Next, an experimental result showing detection amounts of active ingredients obtained through crushing cells obtained by cell culture using the medium composition for cell culture according to the invention will be described. In particular, Example 6, in which an amount of the additive composition is the same as in Embodiment 1, was compared with Embodiment 1.

TABLE 3

| Measurement Type | Group | Control Group | Comparative Example 1 | Embodiment 1 | Embodiment 6 |
|---|---|---|---|---|---|
| | | Detention Amount (Average) | | | |
| After cell crushing | Total Protein (mg/ml) | 50.48 ± 1.07 | 181.12 ± 1.45 | 961.53 ± 2.03 | 2002.13 ± 2.82 |
| After cell crushing | TGF (pg/ml) | 13.06 ± 1.85 | 113.76 ± 2.22 | 124.84 ± 2.01 | 230.90 ± 2.24 |
| After cell crushing | VEGF (pg/ml) | 110.01 ± 3.52 | 350.07 ± 2.68 | 721.04 ± 4.27 | 1902.35 ± 3.59 |
| After cell crushing | KGF (pg/ml) | 9.37 ± 0.25 | 55.63 ± 0.47 | 105.97 ± 0.49 | 460.04 ± 0.52 |
| After cell crushing | Procollagen (ng/ml) | 83.10 ± 1.43 | 261.26 ± 4.61 | 451.10 ± 2.08 | 1498.66 ± 16.42 |

As shown in Table 3, it can be seen that the detection amount of the active ingredients of the cell in Example 6 is high. It can also be expected that detection amounts in Examples 3 to 10, which have the amounts of obtained cells similar or larger than the amount of obtained cells in Embodiment 1, are higher than the detection amounts in Embodiment 1 and Comparative Example 1.

Hereinafter, a test for confirming an anti-arthritic and cartilage regeneration effects on a cartilage cell by a crushed stem cell extract will be described in detail.

1-1. Separation and Culture of Articular Cartilage Cell

Before the test, an cartilage of a female white rat of Wistar rat was collected and cultured in a DMEM medium including 10% FBS (at a culture condition of 37° C. and 5% CO2), and whether an cartilage cell is or not was confirmed by using CD44, which is a specific marker of an cartilage cell.

1-2. Result

The cartilage cell was confirmed by using CD44, which is a specific marker of an cartilage cell.

2-1. Inhibition Effect of Cytotoxic and Nitric Oxide (NO) Generation

1) A cartilage cell was treated with the crushed stem cell extract by concentration and cultured for 24 hours, and cell viability was measured to confirm toxicity to the cell.

2) The cartilage cell was treated with IL-1α to cause inflammation.

3) Inhibition of Nitric Oxide (NO), which is an inflammation mediator, was confirmed by treating the inflammatory cartilage cell with the crushed stem cell extract by concentration.

2-2. Result

1) As a result of measuring the cell viability through the treatment by concentration, there was not cytotoxicity at concentrations up to 20 ng/ml (that is, concentrations of 0, 5, 10, 20 ng/ml).

2) In the cells treated with IL-1α, which is an inflammation inducer, increase in NO was found. As a result of treating the inflammatory cartilage cell with the crushed stem cell extract by concentration, the inflammatory was inhibited by about 30% at a concentration 20 ng/ml (a concentration to the cell that the inflammation is not induced is 20 ng/ml, and concentrations to inflammatory cells are 5, 10, 20 ng/ml)

3-1. Change in iNOS, COX-2 and NF-kB Expression

1) A relationship between NO generation and expression of COX-2 and NF-kB was confirmed by applying Carprofen (non-steroidal substance), which is a positive control group, and the crushed stem cell extract to an IL-1α-treated cartilage cell.

NO: a value increasing when inflammation occurs

COX-2: a king of protein, a material that activity thereof increases by an inflammatory factor and then decreases as inflammation disappears 2) Effect of a treatment to the inflammatory cartilage cell with the crushed stem cell extract on the expression of NF-κB was confirmed.

3-2. Result

1) As a result that the cartilage cell treated with IL-1α to induce inflammation was treated with the crushed stem cell extract, it can be seen that the inhibition effect of the NO generation in the cartilage cell where the inflammation was induced by the IL-1a-treatment is associated with the inhibition of iNOS and COX-2 expression.

2) It can be seen that a migration of an NF-κB protein by IL-1α into a nucleus is inhibited in the cartilage cell treated with the crushed stem cell extract, and thus, a NF-κB pathway, which is a main inflammatory signal pathway induced by IL-1α, can be blocked.

4. Effect on iMAPKs Activity

1) An iMAPKs activity was confirmed by treating the cartilage cell where inflammation was generated by IL-1α with the crushed stem cell extract.

1) Identification of anti-inflammatory mechanism

This indicates that anti-inflammatory effect of the crushed stem cell extract is achieved through inhibition of p38 MAPK signal transmission.

5-1. Measurement of QPCR that is a Factor Involved in Cartilage Cell Formation and Development 1) The anti-inflammatory effect of the stem cell extract was confirmed through genetic expression.

2) The cartilage formation was confirmed by a gene of sox-9 involved in cartilage formation and development.

5-2. Result

1) MMPs are a major protein involved in catabolism of a cartilage tissue. The expression of MMP-13 was greatly increased when IL-1α (inflammation inducing substance) is treated. However, it can be seen that the expression of MMP-13 is reduced when the treatment with the crushed stem cell extract was performed.

2) It can be also seen that the gene expression of SOX-9 involved in cartilage formation and development was increased as an concentration of the crushed stem cell extract treated to the cartilage cell increases.

Hereinafter, a test to confirm an anti-inflammatory effect of a crushed stem cell extract will be described in detail.

1-1. Measurement of Cytotoxicity

1) The crushed stem cell extracts (T-stems) of concentrations of 0.1 μg/ml to 3 μg/ml were treated to mouse macrophages (RAW 246.7) for 24 hours.

2) The crushed stem cell extract and LPS were treated at the same time.

1-2. Result

Figure 10:
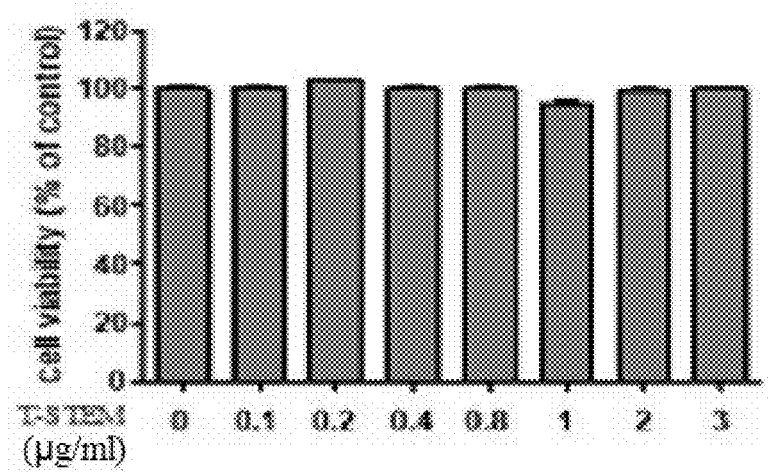
FIG. 10 shows present or absence of cytotoxicity after a treatment with a crushed stem cell extract according to the invention by concentration.

1) As shown in FIG. 10, no statistically significant cytotoxicity was not observed as a result of treatment of the crushed stem cell extract alone by concentration.

Figure 11:
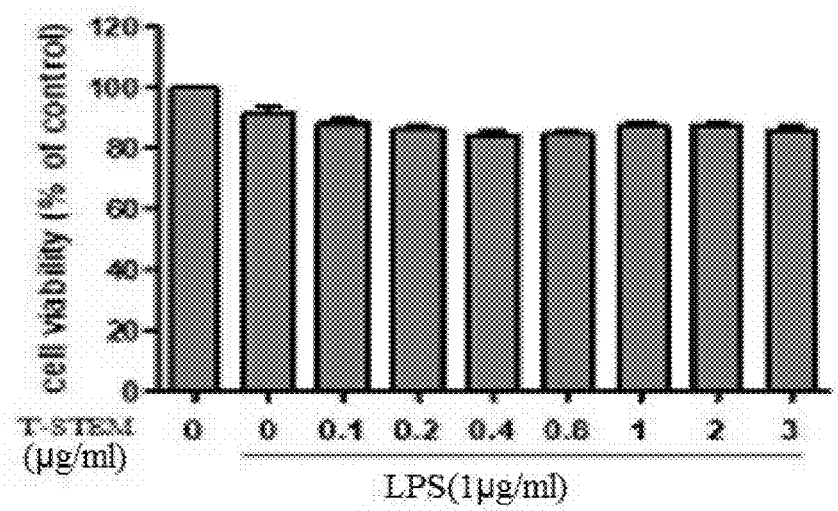
FIG. 11 shows present or absence of cytotoxicity after a treatment with a crushed stem cell extract according to the invention and LPS at the same time.

2) As shown in FIG. 11, when it is treated with 1 μg/ml of Lipopolysaccharide (LPS), which is an inflammatory reaction substance of mouse macrophages, cytotoxicity was not observed after the treatment with the crushed stem cell extract.

2-1. Cell Morphology Change

After 2 μg/ml of the crushed stem cell extract was treated to mouse macrophages (RAW 246.7) for 24 hours, changes in cell morphology were confirmed or checked.

2-2. Result

In a group treated with 1 μg/ml of LPS, which is an inflammation inducer, an activation of macrophages was relatively increased as compared with the control group.

Figure 12:
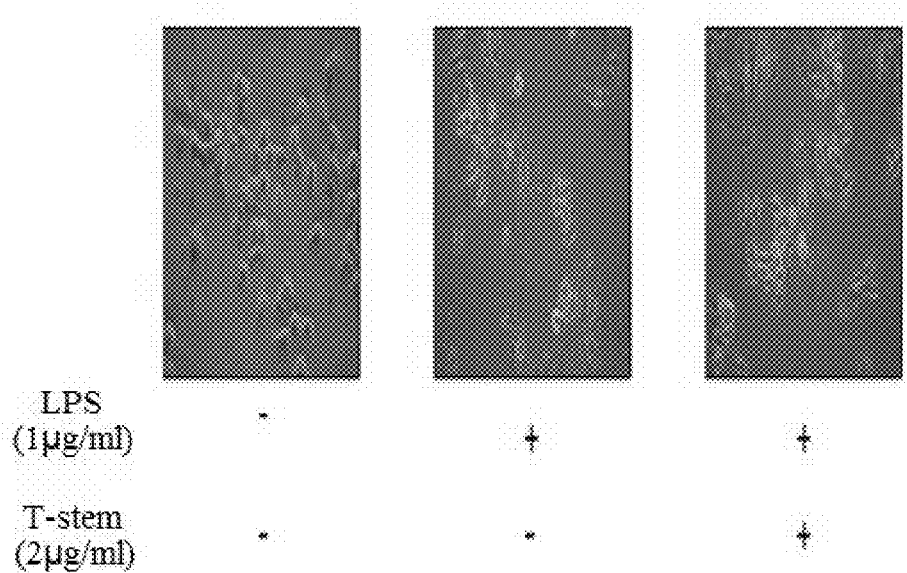
FIG. 12 shows a change in cell morphology after a treatment with a crushed stem cell extract according to the invention and LPS.

As shown in FIG. 12, macrophage activation was relatively less in the cell treated with 1 μg/ml of LPS and the crushed stem cell extract than in the group treated with 1 μg/ml of LPS alone.

3-1. Nitric Oxide

After 0.4 μg/ml to 2 μg/ml of the crushed stem cell extracts were treated for 24 hours to mouse macrophages (RAW 246.7) pretreated with 1 μg/ml of LPS, which is an inflammation inducer, an nitric oxide concentration was measured or confirmed through griess assay.

3-2. Result

A concentration of a nitric oxide was increased by LPS stimulation.

Figure 13:
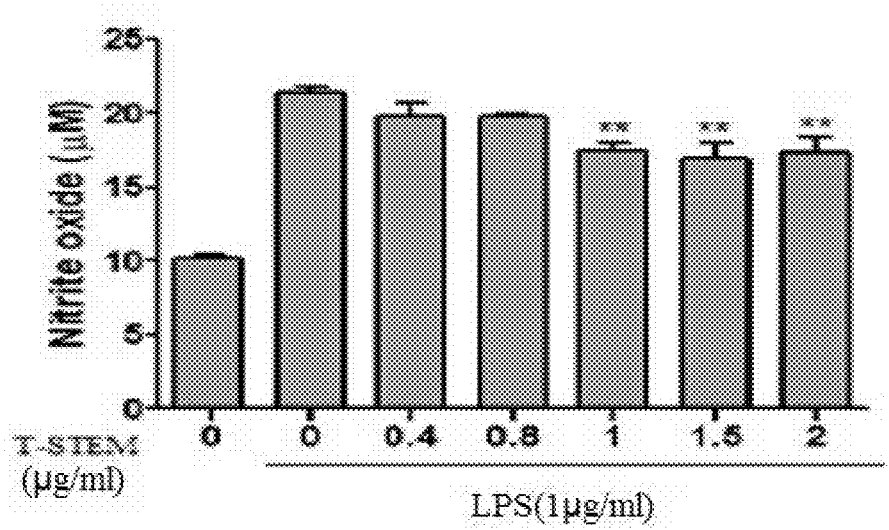
FIG. 13 shows a concentration of a nitric oxide after a treatment with a crushed stem cell extract according to the invention and LPS.

As shown in FIG. 13, a statistically significant decrease in concentration of the nitric oxide was observed in the group treated with LPS and the crushed stem cell extract compared with the group treated with LPS only.

4-1. Changes in iNOS and COX-2 Protein Expression

After 1 μg/ml and 2 μg/ml of the crushed stem cell extracts were treated for 24 hours to mouse macrophages (RAW 246.7) pretreated with 1 μg/ml of LPS, which is an inflammation inducer, expression of iNOS, which is an inflammatory enzyme, and COX-2 protein was measured or confirmed through western blot analysis.

4-2. Result

Figure 14:
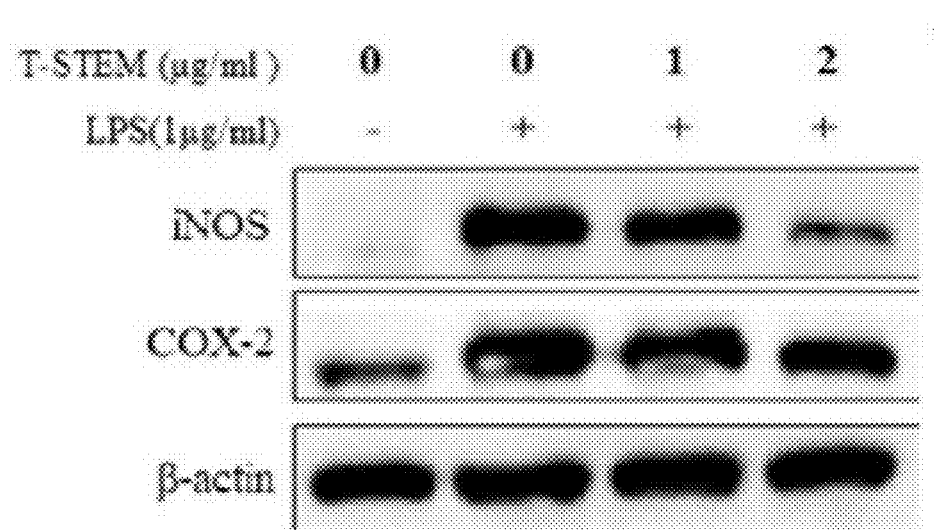
FIG. 14 shows a change in iNOS and COX-2 protein expression by a treatment with a crushed stem cell extract according to the invention and LPS.

As shown in FIG. 14, the expression of iNOS and COX-2 protein was decreased in a concentration-dependent manner in the group treated with the test substance of T-STEM together compared to the group treated with LPS alone.

5-1. Inflammatory Cytokine Production

After 1 μg/ml and 2 μg/ml of the crushed stem cell extracts were treated for 24 hours to mouse macrophages (RAW 246.7) pretreated with 1 μg/ml of LPS, which is an inflammation inducer, a cytokine (TNF α, IL-1β) production was measured or confirmed through ELISA assay.

5-2. Result

It was confirmed that an amount of inflammatory cytokine production was increased by LPS stimulation.

Figure 15:
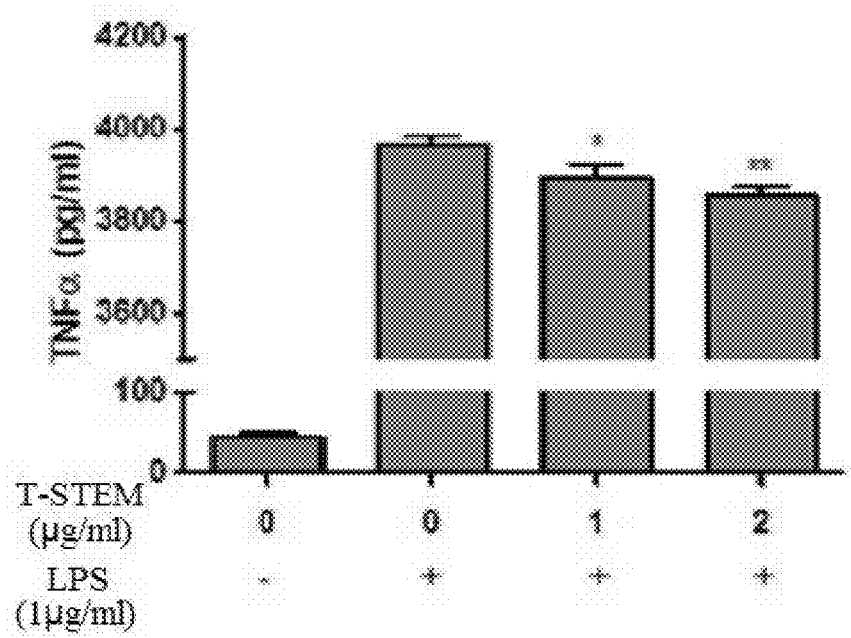
FIG. 15 shows a change in TNFα by a treatment with a crushed stem cell extract according to the invention and LPS.
Figure 16:
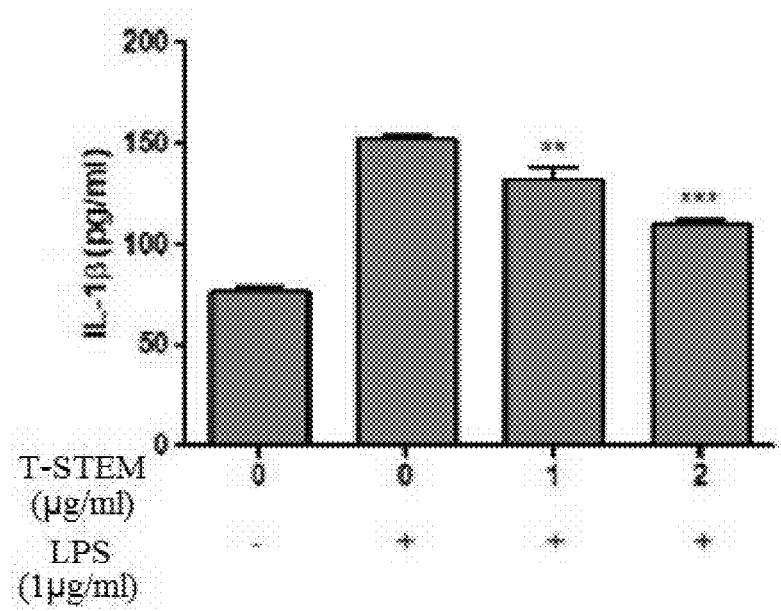
FIG. 16 shows a change in IL-1β by a treatment with a crushed stem cell extract according to the invention and LPS.

As shown in FIGS. 15 and 16, a reduction of inflammatory cytokines was observed by treating the test material of the crushed stem cell extract.

The efficacy of the active ingredients of the crushed stem cell extract according to the invention is as follows.

First, dementia is caused by a degeneration of beta amyloid toxin protein and tau protein. When cord-blood-derived mesenchymal stem cells are repeatedly transplanted into both hippocampus of Alzheimer's disease mouse, a memory capacity is increased, an amount of beta amyloid in the brain is decreased, an amount of β-secretase1, which is an enzyme that produces beta amyloid, is reduced in the brain tissue of mouse, secretion of inflammatory cytokines from microglial cells is suppressed, and secretion of anti-inflammatory cytokines is increased. By the above results, hyperphosphorylation of tau protein can be inhibited.

Therefore, it has been found that the mesenchymal stem cells inhibit a progression of Alzheimer's disease and reduce the amount of beta amyloid toxic protein which is the cause of dementia. The crushed stem cell extract (the shelled stem cell) is a material where active ingredients of a stem cell are concentrated to remove immune rejection, and thus, may be used to treat dementia. Further, since a yield of the cell and yield of the active ingredients are increased according to the invention, it can be used as a therapeutic agent having less risk and excellent effect than using the conventional stem cell itself.

In addition, a gum disease is caused by inflammation of a root of teeth, a bone of the gum, gum, or so on. The crushed stem cell extract according to the invention can help to regenerate the gum and the bone of the gum.

That is, growth factors of the stem cell can be used as a gum treatment or therapy because they help to inhibit inflammation, regenerate a bone, a cartilage, a gum cell, and promote wound healing regeneration. Especially, pro-collagen, a collagen network like a mesh, adheres a cell to another cell firmly, and provides an environment in which cells are made and many parts of a body such as blood vessels, bones, and joints function properly, and thus the crushed stem cell extract can be used as a treatment for the gum disease. Further, since the yield of the cell and the yield of the active ingredients are increased according to the invention, it can be used as a therapeutic agent having less risk and excellent effect than using the conventional stem cell itself.

An arthritis or a periarthritis is caused by inflammation around joints by a problem such as aging and injury. The crushed stem cell extract of the invention can be used as a treatment agent for an arthritis or a periarthritis because it help to inhibit inflammation, regenerate a bone, a cartilage, a cell, and promote wound healing regeneration. Especially, pro-collagen, a collagen network like a mesh, adheres a cell to another cell firmly, and provides an environment in which cells are made and many parts of a body such as blood vessels, bones, and joints function properly, and thus the crushed stem cell extract can be used as a treatment for the arthritis or the periarthritis. Further, since the yield of the cell and the yield of the active ingredient are increased according to the invention, it can be used as a therapeutic agent having less risk and excellent effect than using the conventional stem cell itself.

A cause of hair loss is various, such as environmental factors, genetic factors, or so on. VEGF growth factor of the crushed stem cell extract according to the invention helps hair follicle growth and hair strengthening by stimulating KGF and hair roots, and thus it can be used as a therapeutic agent for the hair loss. Further, since the yield of the cell and the yield of the active ingredients are increased according to the invention, it can be used as a therapeutic agent having less risk and excellent effect than using the conventional stem cell itself.

A cause of skin aging is various, such as environmental factors, genetic factors, or so on. Among the crushed stem cell extract of the invention, KGF can prevent wrinkle and UV simultation, help a skin restoration and a skin protection, and keep a young skin through a new cell production (collagen) function. A collagen network like a mesh adheres a cell to another cell firmly and helps skin elasticity, and thus the crushed stem cell extract can be used as a treatment for a skin. Further, since the yield of the cell and the yield of the active ingredients are increased according to the invention, it can be used as a therapeutic agent having less risk and excellent effect than using the conventional stem cell itself.

It will be understood by those skilled in the art that the technical features of the invention may be embodied in other specific forms without departing from the spirit or essential characteristics thereof.

It is to be understood, therefore, that the embodiments described above are to be considered in all respects as illustrative and not restrictive, the scope of the invention are indicated by the appended claims rather than by the foregoing description, and all changes or modifications that come within the scope of the invention should be construed as being included within the scope of the invention.

What is claimed is:

1. A method of manufacturing a crushed stem cell extract using a method of manufacturing a medium composition for mass culture of a stem cell and a 3-low extracting method of active ingredients of a stem cell, comprising:
    a first step of extracting a stem cell;
    a second step of culturing the extracted stem cell using the medium composition comprising a basal medium, a hyaluronic acid, and an additive composition;
    a third step of subculturing the stem cell;
    a fourth step of obtaining a cell from the cultured stem cell;
    a fifth step of crushing the obtained cell and using an extracting apparatus to extract the active ingredients of the stem cell;
    a sixth step of filtering the crushed material; and
    a seventh step of freeze-dehydrating the filtered material by the sixth step for storing or using the filtered material by the sixth step;
    wherein the extracting apparatus comprises:
        a body portion having an inner space and blocking an inside portion and an outer portion of the body portion;
        a first container provided in the body portion and opened upward;
        a second container having a size smaller than a size of the first container, wherein the second container is provided in the first container and is configured in such a manner that it is opened upward, thereby permitting a stem cell to be inserted into the second container;
        a crushing portion for crushing the stem cell in the second container;
        a valve configured to control or block a flow of air into the body portion; and
        a pump configured to suck a gas in the body portion,
    wherein the fifth step further comprises placing the stem cell into a hypotonic solution and putting the stem cell in the hypotonic solution into the second container, crushing the stem cell in the crushing portion, utilizing the valve to control or block the flow of air into the body portion, and utilizing the pump to suck a gas in the body portion, and
    wherein the additive composition comprises:
        a concentration of hyaluronic acid to the medium composition of 10 μg/ml,
        a concentration of glycine to the medium composition of 1 ng/ml,
        a concentration of histidine to the medium composition of 1 ng/ml,
        a concentration of isoleucine to the medium composition of 1 ng/ml,
        a concentration of methionine to the medium composition of 1 ng/ml,
        a concentration of phenylalanine to the medium composition of 1 ng/ml,
        a concentration of proline to the medium composition of 10 ng/ml,
        a concentration of hydroxyproline to the medium composition of 5 ng/ml,
        a concentration of serine to the medium composition of 1 ng/ml,
        a concentration of threonine to the medium composition of 1 ng/ml,
        a concentration of tryptophan to the medium composition of 1 ng/ml,
        a concentration of tyrosine to the medium composition of 1 ng/ml,
        a concentration of valine to the medium composition of 2 ng/ml,
        a concentration of bFGF to the medium composition of 9 μg/ml,
        a concentration of EGF to the medium composition of 1.5 μg/ml,
        a concentration of VEGF to the medium composition of 1 μg/ml,
        a concentration of KGF to the medium composition of 1.2 μg/ml,
        a concentration of HGF to the medium composition of 0.5 μg/ml,
        a concentration of TGF to the medium composition of 0.5 μg/ml,
        a concentration of vitamin C to the medium composition of 2 μg/ml,
        a concentration of vitamin B1 to the medium composition of 0.5 μg/ml,
        a concentration of vitamin B12 to the medium composition of 3 μg/ml,
        a concentration of vitamin E to the medium composition of 500 μg/ml,
        a concentration of selenium to the medium composition of 1.8 μg/ml, and
        a concentration of transferrin to the medium composition of 12 μg/ml.

* * * * *